United States Patent [19]

Hasenhuettl et al.

[11] Patent Number: 5,424,420
[45] Date of Patent: Jun. 13, 1995

[54] METHOD FOR PREPARING SACCHARIDE POLYESTERS BY TRANSESTERIFICATION

[75] Inventors: Gerry Hasenhuettl, Highland Park; Laura Labeots, Evanston, both of Ill.

[73] Assignee: Kraft Foods, Inc., Northfield, Ill.

[21] Appl. No.: 132,497

[22] Filed: Oct. 5, 1993

[51] Int. Cl.⁶ .................. C07H 1/00; C07H 13/04
[52] U.S. Cl. .................... 536/115; 536/116; 536/119; 536/120; 536/124
[58] Field of Search ............... 536/115, 116, 119, 120, 536/124

[56] References Cited

U.S. PATENT DOCUMENTS

| | | | |
|---|---|---|---|
| 2,853,485 | 9/1958 | Werner et al. | 536/119 |
| 2,893,990 | 7/1959 | Hass et al. | 536/119 |
| 2,931,802 | 4/1960 | Touey et al. | 536/119 |
| 2,938,898 | 5/1960 | Werner et al. | 536/115 |
| 2,948,717 | 8/1960 | Babayan et al. | 536/119 |
| 3,057,743 | 10/1962 | Touey et al. | 536/119 |
| 3,059,009 | 10/1962 | Schmid et al. | 554/208 |
| 3,059,010 | 10/1962 | Schmid et al. | 426/612 |
| 3,093,481 | 6/1963 | Eckey et al. | 536/119 |
| 3,096,324 | 7/1963 | Goins et al. | 536/119 |
| 3,248,381 | 4/1966 | Nobile et al. | 536/119 |
| 3,251,827 | 5/1966 | Schnell et al. | 536/119 |
| 3,353,966 | 11/1967 | Hugenberg et al. | 426/610 |
| 3,378,542 | 4/1968 | O'Boyle et al. | 536/119 |
| 3,480,616 | 11/1969 | Osipow et al. | 536/119 |
| 3,600,186 | 8/1971 | Mattson et al. | 536/119 |
| 3,792,041 | 2/1974 | Yamagishi et al. | 536/119 |
| 3,954,976 | 5/1976 | Mattson et al. | 514/23 |
| 3,963,699 | 6/1976 | Rizzi et al. | 536/119 |
| 4,005,196 | 1/1977 | Jandacek et al. | 514/23 |
| 4,034,083 | 7/1977 | Mattson | 514/53 |
| 4,241,054 | 12/1980 | Volpenhein et al. | 536/115 |
| 4,264,583 | 4/1981 | Jandacek | 514/23 |
| 4,368,213 | 1/1983 | Hollenbach et al. | 426/590 |
| 4,382,924 | 5/1983 | Berling et al. | 536/119 |
| 4,446,165 | 5/1984 | Roberts | 426/602 |
| 4,461,782 | 7/1984 | Robbins et al. | 426/549 |
| 4,517,360 | 5/1985 | Volpenhein | 536/119 |
| 4,518,772 | 5/1985 | Volpenhein | 536/119 |
| 4,611,055 | 9/1986 | Yamamoto et al. | 536/119 |
| 4,675,393 | 6/1987 | Coxon | 536/18.6 |
| 4,840,815 | 6/1989 | Meyer et al. | 426/611 |
| 4,942,054 | 7/1990 | Winter et al. | 426/611 |
| 4,973,489 | 11/1990 | Meyer et al. | 426/611 |
| 5,158,796 | 10/1992 | Bernhardt et al. | 426/549 |

FOREIGN PATENT DOCUMENTS

| | | | |
|---|---|---|---|
| 0349059A2 | 1/1990 | European Pat. Off. | C08G 63/54 |
| 156263 | 2/1981 | German Dem. Rep. | C07H 13/06 |
| 227137A1 | 10/1984 | Germany | C07H 13/06 |
| 262663A1 | 7/1987 | Germany | C07H 13/06 |
| WO92/03060 | 3/1992 | WIPO . | |

OTHER PUBLICATIONS

(Both in German and English) Mieth et al., "On The Synthesis and Characterization of Sucrose Fatty Acid Polyesters." Part 1. On A New Synthesis Procedure [Zur Synthese und charakterisierung von Saccarosefettsäure–polyestern. 1. Mitt. Über ein neues Syntheseverfahren], *Die Nahrung*, pp. 747–751, Aug. 27, 1983.

(List continued on next page.)

*Primary Examiner*—David A. Redding
*Assistant Examiner*—Everett White
*Attorney, Agent, or Firm*—Fitch, Even, Tabin & Flannery

[57] ABSTRACT

An improved method for the preparation of saccharide fatty acid polyesters via an intermolecular transesterification reaction is provided. A saccharide lower acyl ester (for example, sucrose octaacetate) is reacted with a fatty acid lower alkyl ester (for example, methyl stearate) in the presence of an alkali metal alkoxide catalyst to produce a saccharide fatty acid polyester. The reaction is carried out at relatively low temperatures in the absence of solvent. The relatively low molecular weight by-produce ester is removed from the reaction mixture during the course of the reaction in order to drive the equilibrium transesterification reaction to completion. The saccharide fatty acid polyesters are useful as fat substitutes or low-calorie fats in food compositions.

44 Claims, No Drawings

OTHER PUBLICATIONS

Akoh et al., "Preparation of Trehalose and Sorbitol Fatty Acid Polyesters by Interesterification", *JAOCS*, vol. 66, No. 9, (Sep. 1989), pp. 1581–1587.

Akoh et al., "Optimized Synthesis of Sucrose Polyesters: Comparison of Physical Properties of Sucrose Polyesters, Raffinose Polyesters and Salad Oils", *Journal of Food and Science*, vol. 55, No. 1, 1990.

Akoh et al., "Synthesis and Properties of Alkyl Glycoside and Stachyose Fatty Acid Polyesters", *JAOCS*, vol. 66, No. 9 (Sep. 1989), pp. 1295–1301.

Akoh et al., "One-Stage Synthesis of Raffinose Fatty Acid Polyesters", *Journal of Foods and Science*, vol. 52.

Linstead et al., "The Stable Form of Sucrose Octaacetate", *J. Amer. Chem. Soc.*, 62, 3260 (1940).

METHOD FOR PREPARING SACCHARIDE POLYESTERS BY TRANSESTERIFICATION

FIELD OF THE INVENTION

This invention provides an improved method for the preparation of saccharide fatty acid polyesters, especially sucrose fatty acid polyesters, via an intermolecular transesterification reaction of the acyl ester or hydroxyl groups of a saccharide with a fatty acid ester or esters. The improved method of this invention essentially eliminates or reduces the hazards (i.e., fire or explosion) associated with the use of molten alkali metal catalysts in the prior one-step, solvent-free transesterification reaction methods used for the production of saccharide fatty acid polyesters. Additionally, the improved method of this invention provides for more rapid conversion to the desired products and provides products having better (i,e,, lighter) color characteristics. The sucrose fatty acid polyesters produced by the improved method of this invention are especially useful as fat substitutes in food applications and products.

BACKGROUND OF THE INVENTION

The human consumption of fats in various foodstuffs contributes significantly to obesity. High fat diets also contribute to various human diseases such as heart and coronary diseases. One method of reducing obesity and/or diseases such as heart and coronary diseases in the human population is to reduce the consumption of fat. In recent years, fat substitutes or low-calorie fats have attracted increasing attention as a method of reducing the fat and calorie content of foodstuffs. The objective is to provide edible fats with reduced absorption and digestive properties with minimal side effects and with acceptable taste and feel characteristics when incorporated into food compositions.

Transesterification reactions have been used to prepare saccharide polyesters with reduced absorption and digestive properties. Such transesterification reactions generally required high temperatures and/or toxic solvents (such as dimethylacetamide, dimethylformamide, dimethylsulfoxide, and the like) and were not, therefore, generally suitable for the preparation of fat substitutes for use in food applications.

More recently, Meyer et al., U.S. Pat. No. 4,840,815 (issued Jun. 20, 1989), and Meyer et al., PCT Publication WO 92/03060 (published Mar. 5, 1992), provided a one-stage, solvent-free, low-temperature, low-pressure process for the preparation of saccharide fatty acid polyesters. The Meyer et al. process involves reacting a mixture of a lower acyl ester saccharide, a fatty acid lower alkyl ester, and an alkali metal catalyst at a reaction temperature of 100° to 125° C. while drawing a vacuum of less than about 15 torr over the reaction mixture. The saccharide fatty acid polyesters are reported to be formed via a transesterification reaction whereby at least a portion of the lower acyl ester groups on the starting saccharide are replaced with the fatty acid groups from the fatty acid lower alkyl ester. The transesterification catalysts employed were alkali metals, with sodium and potassium metals the most preferred. At the reaction temperature, the alkali metal catalysts were molten.

In addition to the transesterification catalysts used by Meyer et al. (i.e., elemental alkali metals), other basic transesterification catalysts are known for the preparation of saccharide fatty acid esters from the saccharides. Such basic transesterification catalysts include alkali metal carbonates, alkali metal hydroxides, and alkali metal alkoxides. None of the just-mentioned catalysts have been used in the Meyer et al. method.

Yamamoto et al., U.S. Pat. 4,611,055 (issued Sep. 9, 1986), report that the alkali metal carbonate and alkali metal hydroxide catalysts generally provide higher yields than the alkali metal alkoxide catalysts. Volpenhein, U.S. Pat. 4,517,360 (issued May 14, 1985), reports that the alkali metal carbonate catalysts provide increased yields and shorter reaction times than the alkali metal hydroxide and alkali metal alkoxide catalysts. These basic transesterification catalysts (i.e., alkali metal carbonates, hydroxides, and alkoxides) generally require higher reaction temperatures (on the order of 180° C.) than the alkali metal catalysts of Meyer et al. Moreover, the transesterification methods and catalysts of Yamamoto et al. and Volpenhein generally require a fatty acid metal soap to insure a homogeneous reaction mixture. Such fatty acid metal soaps are not used or required in the Meyer et al. method. Mieth et al., German Patent 227,137 A1 (laid open Sep. 11, 1985), provides a method for preparing polyol-ester mixtures suitable for use as fat substitutes whereby saccharides are esterified or transesterified with short-chain carboxylic acid derivatives in the presence of a catalyst and then reacted with triglycerides having long-chain carboxylic acid derivatives (i.e., pig grease or hard rape fat) at a temperature of 120° to 140° C. The polyol-ester mixtures so produced can be subjected to further transesterification reactions at 100° to 120° C. using long-chain carboxylic acids or their esters as reagents. The catalysts used by Mieth et al. include phosphorous acid, alkali metals, alkali alkylates, and alkali salts of weak acids.

Based on the prior art, it was surprising to discover, as explained in the present application, that alkali metal alkoxides can be used as catalysts for the preparation of saccharide fatty acid polyesters, especially sucrose fatty acid polyesters, using the general procedure of Meyer et al. (i.e., lower reaction temperatures without added fatty acid metal soaps). Moreover, it was even more surprising to discover that alkali metal alkoxide catalysts provide an improved process over that of the Meyer et al. process using alkali metal catalysts. The improved method of this invention essentially eliminates or reduces the hazards (i.e., fire or explosion) associated with the use of molten alkali metals in the Meyer et al. transesterification reaction method, provides for more rapid conversion to the desired products than the Meyer et al. transesterification reaction method, and provides products having better (i.e., lighter) color characteristics than the Meyer et al. transesterification reaction method. The methods of the present invention are generally easier to use and provide better saccharide polyesters than the methods of the prior art.

SUMMARY OF THE INVENTION

The present invention relates to an improved method for preparing saccharide fatty acid polyesters, especially sucrose fatty acid polyesters, via an intermolecular transesterification reaction. The improved method of this invention essentially eliminates or reduces the hazards (i.e., fire or explosion) associated with the use of molten alkali metals in prior transesterification reaction methods used for the production of saccharide fatty acid polyesters. Additionally, the improved method of this invention provides for more rapid conversion to the desired products and provides products having better (i.e., lighter) color characteristics. The sucrose fatty acid polyesters produced by the improved method of this invention are especially useful as fat substitutes in food applications and products.

The improved process of the present invention involves the reaction of a lower acyl ester saccharide, a fatty acid lower alkyl ester, and an alkali metal catalyst under essentially anhydrous conditions to effect a transesterification reaction whereby a portion of the lower acyl ester groups Of the saccharide are effectively replaced by the fatty acid groups of the fatty acid lower alkyl esters. The lower acyl ester saccharide reactant should be treated prior to reaction to remove or significantly reduce moisture and free organic acid; the fatty acid lower alkyl ester reactants should be treated to remove or significantly reduce moisture. The catalysts are preferably freshly prepared for the highest product yield. The transesterification reaction is carried out at temperatures of from about 95° to 125° C. under essentially anhydrous conditions while the relatively low molecular weight, non-fatty acid-containing lower alkyl ester by-product is removed from the reaction system to drive the reaction equilibrium towards the formation of the desired saccharide fatty acid polyester. The reaction can be illustrated by the following general reaction scheme:

$$(RC(=O)OCH_2)_n(RC(=O)O)_mX + R'COOR'' \xrightarrow{catalyst}$$

$$(R'C(=O)OCH_2)_n(R'C(=O)O)_mX + (RCOOR'')\uparrow$$

where RC(=O)— represents a lower acyl group where R is an alkyl group having less than 6 carbon atoms, X represents the saccharide backbone, n is the number of ester groups on the primary carbons in the saccharide backbone, m is the number of ester groups on the secondary carbons of the saccharide backbone, R' is a saturated or unsaturated long chain aliphatic group preferably derived from a fatty acid, R'' is a lower alkyl group having less than six carbon atoms, and the catalyst is an alkali metal. alkoxide. The by-product RCOOR'' is removed from the reaction mixture (as indicted by the ↑ in the above equation) in order to drive the equilibrium towards the desired saccharide fatty acid polyester product $(R'COOCH_2)_n(R'COO)_mX$. Preferably R and R'' are methyl groups, in which case the by-product RCOOR'' is methyl acetate. Using the preferred sucrose octaacetate, a fatty acid methyl ester ($R'COOCH_3$ where R' is an aliphatic group derived from a long chain fatty acid), and sodium methoxide catalyst as an example, the general transesterification reaction scheme can be illustrated as follows:

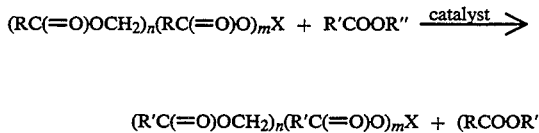

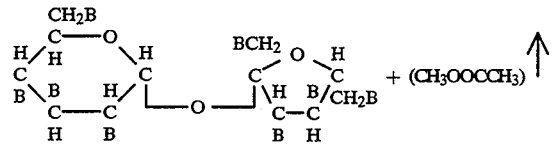

where A is a —OOCCH₃ group and B is a —OOCR' group. The by-product methyl acetate is removed from the reaction mixture to drive the equilibrium to the right hand side of the equation and towards formation of the sucrose fatty acid polyester.

In another embodiment of the present invention, the fatty acid lower alkyl ester (or mixture of fatty acid lower alkyl esters) and the alkali metal alkoxide are first reacted under essentially anhydrous conditions at about 95° to 125° C. before the addition of the lower acyl ester saccharide. After the lower acyl ester saccharide is added, the reaction is continued at about 95° to 125° C. for a time sufficient to form the saccharide fatty acid polyester, while removing the relatively low molecular weight, non-fatty acid-containing lower alkyl ester by-product from the reaction mixture.

One object of the present invention is to provide a method for making a saccharide fatty acid polyester comprising:
(1) esterifying hydroxyl groups of a saccharide to form a lower acyl ester saccharide;
(2) treating the lower acyl ester saccharide to reduce the level of free organic acid therein to less than about 0.25 weight percent;
(3) mixing the treated lower acyl ester saccharide, a fatty acid lower alkyl ester, and an alkali metal alkoxide catalyst under essentially anhydrous conditions to form a reaction mixture; and
(4) heating the reaction mixture to about 95° to 125° C., while removing a non-fatty acid-containing lower alkyl ester by-product from the reaction mixture, for a time sufficient to form the saccharide fatty acid polyester.

Another object of the present invention is to provide a method for making a saccharide fatty acid polyester comprising:
(1) mixing a lower acyl ester saccharide, a fatty acid lower alkyl ester, and an alkali metal alkoxide catalyst under essentially anhydrous conditions to form a reaction mixture, wherein the lower acyl ester saccharide has less than about 0.25 weight percent free organic acid; and
(2) heating the reaction mixture to about 95° to 125° C., while removing a non-fatty acid-containing lower alkyl ester by-product from the reaction mixture, for a time sufficient to form the saccharide fatty acid polyester.

Another object for the present invention is to provide a method for making a saccharide fatty acid polyester comprising:
(1) mixing a fatty acid lower alkyl ester and an alkali metal alkoxide catalyst under essentially anhydrous conditions to form a first reaction mixtures;
(2) heating the first reaction mixture to about 50° to 125° C.;
(3) adding an essentially anhydrous lower acyl ester saccharide having less than about 0.25 weight percent: free organic acyl acid to the first reaction mixture from step (2) to form a second reaction mixture; and (4) heating the second reaction mixture to about 95° to 125° C., while removing a non-fatty acid-containing lower alkyl ester by-product from the second reaction mixture, for a time sufficient to form the saccharide fatty acid polyester.

Still another object of the present invention is to provide a method for making a saccharide fatty acid polyester comprising:

(1) mixing a lower acyl ester saccharide having less than about 0.25 weight percent free organic acid, a fatty acid lower alkyl ester, and an alkali metal alkoxide catalyst under essentially anhydrous conditions to form a reaction mixture; and (2) heating the reaction mixture to about 95° to 125° C. for a time sufficient to form the saccharide fatty acid polyester, while removing a non-fatty acid-containing lower alkyl ester by-product from the reaction mixture by inert gas stripping.

These and other objects and advantages of the present invention will become apparent through the following description of the preferred embodiments of the invention.

DESCRIPTION OF THE PREFERRED EMBODIMENTS

The method of the present invention provides an improved method for the preparation of saccharide fatty acid polyesters via a transesterification reaction. The present method provides a solvent-free, single-step synthesis whereby a lower acyl ester saccharide and a fatty acid lower alkyl ester are reacted under essentially anhydrous conditions in the presence of an alkali metal alkoxide catalyst at a temperature of about 95° to 125° C. At the reaction temperature, the reactants will generally form a homogeneous reaction mixture. The relatively low molecular weight, non-fatty acid-containing lower alkyl ester by-product is continuously removed in order to drive the reaction equilibrium towards completion and the formation of the desired saccharide fatty acid polyester. Generally yields on the order of about 80 to 99 percent can be obtained with reaction times of about four hours.

The method of the present invention involves modifications and improvements of the general method described in Meyer et al., U.S. Pat. 4,840,815 (issued Jun. 20, 1989), and Meyer et al., PCT Publication WO 92/03060 (published Mar. 5, 1992), both of which are hereby incorporated by reference.

The lower acyl ester saccharide can be prepared by conventional means by esterifying the hydroxyl groups of a saccharide. One such conventional esterification method for preparing lower acyl ester saccharides is described in Linstead et al., *J. Amer. Chem. Soc.*, 62, 3260 (1940). By "lower acyl" group it is meant an acyl group of formula $RC(=O)-$ where R is an alkyl group having less than 6 carbon atoms. The lower acyl ester saccharides can be represented by the general formula $(RC(=O)OCH_2)_n(RC(=O)O)_mX$ where R is an alkyl group having less than six carbon atoms, n is the number of primary carbon atoms in the saccharide backbone having ester groups, m is the number of secondary carbon atoms in the saccharide backbone having ester groups, and X generally represents the saccharide backbone. Prior to use in this invention, the lower acyl ester saccharide should be treated to significantly reduce the moisture content and free organic acid content. Generally the free organic acid content of the lower acyl ester saccharide should be reduced to less than about 0.25 weight percent, more preferably to less than about 0.1 weight percent, and most preferably to less than about 0.05 weight percent. Conventional methods to remove moisture and free organic acids can be used. One preferred technique whereby water and free organic acids are removed in a single step is freeze drying.

The saccharide starting materials for the present invention can be monosaccharides, disaccharides, and higher polysaccharides. Suitable monosaccharides include fructose, glucose, galactose, mannose, ribulose, rhamnose, xylulose, xylose, ribose, and arabinose; glucose is the preferred monosaccharide. Suitable disaccharide include melibiose, lactose, maltose, sucrose, trehalose, and cellobiose; sucrose is the preferred disaccharide. Suitable higher polysaccharides include raffinose, gentianose, 4'-galactosyl lactose, trisaccharides of galactose, mannose, glucose, and fructose, stachyose, verbascose, maltodextrins, corn syrup solids, zylans, glycogen, cellulose, amylose, agarose, galactans, and mannans. Sucrose, a non-reducing disaccharide, is the most preferred starting saccharide.

As noted above, the saccharide starting materials are converted to the lower acyl ester saccharide by esterifying the hydroxyl groups of the saccharide starting materials using conventional methods. This initial esterification can be carried out as a separate step or can be incorporated into the process of the present invention. Non-reducing saccharides (such as sucrose) can be converted directly into the lower acyl ester saccharides. Reducing saccharides (having a hydroxyl group alpha to an ether linkage) must first be converted to a non-reducing form prior to the initial esterification reaction; such conversion can be carried out using conventional means. For example, a reducing saccharide can be converted to a non-reducing saccharide by reaction with an alcohol to form a glycoside. Suitable alcohols for converting the reducing saccharides to non-reducing saccharides include, for example, alkyl alcohols, aryl alcohols, alkaryl alcohols, aralkyl alcohols, alkaryl alcohols, heteroalkyl alcohols, heteroaryl alcohols, thio alcohols, and polyalcohols including sugar alcohols. Preferred alcohols are alkyl alcohols containing 1 to 6 carbon atoms with methanol and ethanol being most preferred. Thus, the reducing saccharide glucose can be converted to the non-reducing methyl glucoside by reaction with methanol in the presence of HCl whereby the hydroxyl group alpha to the ether linkage is methylated. Once the non-reducing saccharide is formed, the remaining hydroxy groups may then be esterified in the normal manner to form the lower acyl ester saccharides.

Both naturally-occurring non-reducing saccharides and non-reducing saccharides prepared from reducing saccharides are employed in the same manner in the present invention. At least 50 percent of the available hydroxyl groups in the saccharide must be converted to ester groups for the saccharide to be useful in the present invention. Preferably, all available hydroxyl groups in the saccharide are converted to ester groups.

Preferred lower acyl ester saccharides are derived from sucrose and have eight ester groups of the general formula —OOCR, where R is an aliphatic group containing from 1 to 6 carbon atoms, attached to the sucrose backbone in place of the hydroxy groups. The most preferred lower acyl ester saccharide is sucrose octaacetate.

The fatty acid lower alkyl esters employed in the present invention are of general formula R'COOR" where R' is a saturated or unsaturated aliphatic group generally containing from 3 to about 24 carbon atoms and R" is a lower alkyl group having from 1 to about 6 carbon atoms. Preferably, R' is a long chain saturated or unsaturated aliphatic group containing between about 8 to 24 carbon atoms. Most preferably, R' is a long chain saturated or unsaturated aliphatic group containing between about 12 to 22 carbon atoms and R" is a methyl group. The fatty acid lower alkyl esters are preferably derived from the corresponding fatty acids. Examples of suitable fatty acids for forming the fatty acid lower alkyl esters include butyric, caproic, caprylic, capric, lauric, myristic, myristoleic, palmitic, palmitoleic, stearic, oleic, ricinoleic, linoleic, oleosteric, arachidic, behenic, erucic, arachidonic, and lignoceric acids. Generally fatty acids containing between about 14 and 18 carbon atoms are preferred since they are liquid at the reaction temperature and the corresponding fatty acid lower alkyl esters formed therefrom have minimal volatility at the reaction temperature and conditions employed in the esterification reaction. Pure fatty acids or naturally-occurring fats and oils (such as, for example, found in soybean, safflower, corn, peanut, and cottonseed oils) can be used. Partially hydrogenated natural fats and oils are particularly suited for use in this invention. The fatty acids can be converted to the corresponding fatty acid lower alkyl esters using conventional methods. Both single fatty acid lower alkyl esters or mixtures of fatty acid lower alkyl esters may be employed in the present invention. Preferred fatty acid lower alkyl esters include methyl stearate, methyl oleate, methyl palmitate, methyl laurate, methyl linoleate, and mixtures thereof.

Generally, the fatty acid lower alkyl esters and the lower acyl ester saccharide are present in the reaction mixture at a molar ratio of at least about 4 to 1 and preferably at a molar ratio of between about 6 to 1 and 15 to 1. Of course, the desired molar ratio will vary with different lower acyl ester saccharides because of the different number of ester groups present. More preferably, the amounts of the lower acyl ester saccharide and the fatty acid lower alkyl esters in the reaction mixture are adjusted so that the molar ratio of the fatty acid lower alkyl esters to the lower acyl ester saccharide is about equal to the number of available ester groups in the lower acyl ester saccharide. For example, when using sucrose octaacetate (with eight available ester groups), the molar ratio of the fatty acid lower alkyl ester to the lower acyl ester saccharide would preferably be about 8 to 1 (i.e., approximately one fatty acid lower alkyl ester molecule for each available ester group in the saccharide). Lower or higher molar ratios can be used if desired within the general guidelines provided above.

The catalysts employed in the present invention are the alkali metal alkoxides. The sodium and potassium alkoxides are generally preferred. Preferred catalysts include potassium methoxide, sodium methoxide, potassium ethoxide, sodium ethoxide, potassium t-butoxide, and sodium t-butoxide. Mixtures of catalysts can also be used. Sodium methoxide is generally most preferred in the practice of the present invention. The catalyst is generally used in an amount less than about 5 weight percent and preferably in the range of about 1 to 2.5 weight percent. For the highest product yields, the catalyst should be freshly prepared.

The reaction mixture formed from the basic starting materials (lower acyl ester saccharide, fatty acid lower alkyl ester, and alkali metal alkoxide) should be essentially anhydrous. Additionally, as noted above, the lower acyl ester saccharide should be essentially free of organic acids. The reaction itself is also carried out under essentially anhydrous conditions. Conventional means can be used to insure the required essentially anhydrous reactants and conditions. For example, reactants can be vacuum dried and stored over phosphorous pentoxide or other drying agents. The lower acyl ester saccharide can be freeze dried to remove both water and free organic acids. The reaction apparatus can be dried by flushing with dried, inert gases.

In one embodiment, the reactants (lower acyl ester saccharide, fatty acid lower alkyl ester, and alkali metal alkoxide) are mixed in a reaction vessel and then heated to the reaction temperature (about 95° to 125° C.). As the transesterification reaction proceeds, the relatively low molecular weight, non-fatty acid-containing lower alkyl ester by-product is removed to drive the equilibrium transesterification to completion. Preferably the by-product ester is removed by vacuum techniques or by inert gas stripping or sparging.

In another embodiment, only the fatty acid lower alkyl ester and the alkali metal alkoxide are initially mixed in the reaction vessel and then heated to an elevated temperature (about 50° to 125° C.). After holding at this elevated temperature for a relatively short time (generally about one-half to one hour), the lower acyl ester saccharide is added and the reaction is continued at the reaction temperature of about 95° to 125° C. As the transesterification reaction proceeds, the relatively low molecular weight, non-fatty acid-containing lower alkyl ester by-product is removed to drive the equilibrium transesterification to completion. Preferably the by-product is removed by vacuum techniques or inert gas stripping or sparging.

Except for the order of addition of the reactants and the initial reaction time without any lower acyl saccharide present, the two just-mentioned processes or embodiments are carried out in essentially the same manner with the same reactants and reaction conditions. Preferably the transesterification reactions of this invention are carried out in batch or semi-batch process.

In still another embodiment, an alkaline earth hydride co-catalyst or an alkali metal hypophosphite co-catalyst is used in combination with the alkali metal alkoxide catalyst. The use of such alkaline earth hydride co-catalyst generally provides a lighter colored polyester product. The use of such alkali metal hypophosphite co-catalyst generally provides a higher yield of the polyester product. The preferred alkaline earth hydride co-catalyst is calcium hydride and the preferred alkali metal hypophosphite co-catalyst is sodium hypophosphite. Preferably the co-catalysts are used in conjunction with the preferred sodium methoxide catalyst. When used, the co-catalyst is generally in the range of about 0.1 to about 2.5 weight percent. It is also generally preferred that the co-catalyst, when used, is added prior to the alkali metal alkoxide catalyst. Otherwise, the reactions and procedures are generally carried out in a manner similar to those used with the alkali metal alkoxide alone.

As noted above, the relatively low molecular weight, non-fatty acid-containing lower alkyl ester by-product is removed (preferably continuously) during the transesterification reaction to drive the equilibrium towards the desired saccharide fatty acid polyester. Preferably, the reactants are selected so that the relatively low molecular weight, non-fatty acid-containing lower alkyl ester by-product (such as methyl acetate) is relatively volatile and, thus, can be removed relatively easily from the reaction mixture.

One preferred method of removing the by-product ester is to continuously draw a vacuum over the reaction mixture. Another preferred method of removing the by-product ester is inert gas stripping or sparging; suitable inert gases include nitrogen, argon, and the like. Vacuum techniques, however, generally provide higher product yields. When using vacuum to remove the by-product ester, it is generally preferred that the pressure is less than about 500 mm Hg, preferably less than about 250 mm Hg, more preferably less than about 15 mm Hg, and most preferably less than about 1 mm Hg. When using inert gas stripping, the pressure can be at atmospheric pressure as well as below or above atmospheric pressure. Most preferably, the reaction is run under an inert, reduced-pressure, stream of nitrogen or argon at a vacuum lower than about 1 mm Hg. It is also generally preferred that the vacuum and inert atmosphere be initiated before the reactants are heated to the desired reaction temperature. Generally, as noted above, the reaction temperature is in the range of about 95° to 125° C.; preferably, the reaction temperature is in the range of about 105° to 115° C.

The reaction is continued until sufficient conversion of the lower acyl ester saccharide to the desired saccharide fatty acid polyester has occurred. Generally a reaction time of about four hours will result in a 80 to 99 percent conversion to the desired product. Once the transesterification reaction is completed, the reaction mixture is allowed to cool and the saccharide fatty acid polyester is collected and, if desired, purified. Conventional purification techniques can be used. It is generally preferred that the reaction mixture is first neutralized (using, for example, acetic acid), dissolved in an organic solvent (for example, hexane), and treated with activated carbon. Alternatively, the saccharide fatty acid polyester can be decolorized using hydrogen peroxide. After removing any added carbon or organic solvents, the desired saccharide fatty acid polyester can be obtained using conventional techniques included, but not limited to, molecular or short-path distillation.

Generally, the saccharide fatty acid polyesters produced by this invention are useful as fat substitutes or low-calorie fats. It is generally preferred that essentially all of the ester groups in the saccharide fatty acid polyesters have fatty acid derived groups. The saccharide fatty acid polyesters of the present invention are especially useful as fat substitutes or low-calorie fats in food products intended for human consumption. These saccharide fatty acid polyesters may be blended or incorporated into food compositions to reduce the overall calorie content of prepared food product. Liquid, semisolid, or solid saccharide fatty acid polyesters (or combinations thereof) may be employed as fat substitutes. The solid saccharide fatty acid polyesters (i.e., melting points above about 37° C.) may also function as antianal leakage agents for use with the liquid saccharide fatty acid polyesters of this invention.

The following examples are provided to illustrate the invention and not to limit the invention. Unless specified otherwise, all percentages given in this specification are by weight.

EXAMPLE 1

A reaction vessel was flushed with dry nitrogen gas for approximately ten minutes prior to the introduction of the reactants. Methyl stearate (29.85 g; 0.1 moles) and methyl oleate (29.65 g; 0.1 moles) were added and stirred under vacuum at 50° C. for one-half hour. Sucrose octaacetate (16.97 g; 0.025 moles) was added and stirring was continued at 50° C. under vacuum for one-half hour. Sodium methoxide (1.52 g; 2 weight percent) was then added. The molar ratio of fatty acid methyl esters to sucrose octaacetate was about 8 to 1. All reactants were essentially anhydrous; the sucrose octaacetate was freeze dried prior to use in order to remove residual moisture and free acetic acid. While drawing a vacuum of about 0.5 mm Hg, the reactants were heated to about 110° C. to form a homogeneous reaction mixture. At the reaction temperature, the reaction mixture began to bubble indicating that the reaction by-product was being foiled. The reaction mixture turned a light brown color. The reaction was continued for about four hours during which time by-product methyl acetate was continuously removed. The cooled product was washed with a hexane and methanol mixture (4 to 1 ratio) containing about 5 weight percent glacial acetic acid and collected. The final product (65 g; 85 percent yield) was a light tan saccharide fatty acid polyester. Thin layer chromatography (TLC) indicated that the transesterification reaction was essentially complete with negligible residual starting materials remaining.

The yield of the desired saccharide fatty acid polyester was 85 percent as determined from high performance liquid chromatography (HPLC). The yield from this example was significantly higher than from similar preparations under similar conditions using sodium metal as the catalyst (66 percent yield) or potassium carbonate as the catalyst (37 percent yield). The color of the final saccharide fatty acid polyester from this example was also much lighter than that of a similar saccharide fatty acid polyester product prepared under similar conditions using sodium metal as the catalyst. The increased purity of the present saccharide fatty acid polyester (as compared to products prepared using alkali metal catalysts) is especially important and significant as these saccharide fatty acid polyesters are to be used as fat substitutes or low-calorie fats in food applications.

EXAMPLE 2

A reaction vessel was flushed with dry nitrogen gas for approximately ten minutes prior to the introduction of the reactants. Methyl stearate (29.85 g; 0.1 moles) and methyl oleate (29.65 g; 0.1 moles) were added and stirred at 0.5 mm Hg at 50° C. for one-half hour. Sodium methoxide (1.52 g; 2 weight percent) was added, stirred, and heated to 50° C. at 0.5 mm Hg for one hour. Sucrose octaacetate (16.97 g; 0,025 moles) was then added. The molar ratio of fatty acid methyl esters to sucrose octaacetate was about 8 to 1. All reactants were essentially anhydrous; the sucrose octaacetate was freeze dried prior to use to remove residual moisture and free acetic acid. While drawing a vacuum of about 0.5 mm Hg, the reactants were heated to about 110° C. to form a homogeneous reaction mixture. The reaction was allowed to continue for about four hours at which time the product was collected as in Example 1. The yield of the sucrose polyester was about 82 percent as determined HPLC.

EXAMPLE 3

A reaction vessel was flushed with dry nitrogen gas for approximately ten minutes prior to the introduction of the reactants. A blend of methyl esters (1103.77 g;

3.75 moles) containing methyl oleate, methyl stearate, methyl linoleate, and methyl palmitate in a 20:50:20:10 weight ratio were stirred and heated to 50° C. at 0.5 mm Hg for one-half hour. Sucrose octaacetate (16.97 g; 0.025 moles) was added and the reaction mixture was stirred and heated to 50° C. at 0.5 mm Hg for an additional one-half hour. The ratio of fatty acid methyl esters to sucrose octaacetate was about 8 to 1. Sodium methoxide (28.73 g; 2 weight percent) was added and the reaction mixture was heated to 110° C. with stirring under a vacuum of 0.5 mm Hg for about six hours. All reactants were essentially anhydrous; the sucrose octaacetate was freeze dried prior to use to remove residual moisture and free acetic acid. The product sucrose polyester was collected as in Example 1. The yield of the sucrose polyester was about 82 percent as determined by HPLC.

EXAMPLE 4

A reaction vessel was flushed with dry nitrogen gas for approximately ten minutes prior to the introduction of the reactants. Methyl stearate (29.85 g; 0.1 moles) and methyl oleate (29.65 g; 0.moles) were added and stirred at 233 mm Hg at 50° C. with nitrogen gas sparging for one-half hour. Sucrose octaacetate (16.97 g; 0.025 moles) was then added and stirred under the same conditions for an additional one-half hour. The molar ratio of fatty acid methyl esters to sucrose octaacetate was about 8 to 1. Sodium methoxide (1.53 g; 2 weight percent) was added. The reaction mixture was stirred and heated to 110° C. at 233 mm Hg for about five hours with continuous nitrogen gas sparging to remove the by-product methyl acetate. All reactants were essentially anhydrous; the sucrose octaacetate was freeze dried prior to use to remove residual moisture and free acetic acid. The yield of the sucrose polyester was about 78 percent as determined by HPLC.

EXAMPLE 5

A reaction vessel was flushed with dry nitrogen gas for approximately ten minutes prior to the introduction of the reactants. Methyl stearate (29.85 g; 0.1 moles) and methyl oleate (29.65 g; 0.1 moles) were added and stirred at 50° C. and atmospheric pressure with nitrogen gas sparging for one-half hour. Sucrose octaacetate (16.97 g; 0.025 moles) was then added and stirred under the same conditions for an additional one-half hour. The molar ratio of fatty acid methyl esters to sucrose octaacetate was about 8 to 1. Sodium methoxide (1.53 g; 2 weight percent) was added. The reaction mixture was stirred and heated to 110° C. at atmospheric pressure for about four hours with continuous nitrogen gas sparging to remove the by-product ester. All reactants were essentially anhydrous; the sucrose octaacetate was freeze dried prior to use to remove residual moisture and free acetic acid. The yield of the sucrose polyester was about 62 percent as determined by HPLC.

EXAMPLE 6

A reaction vessel was flushed with dry nitrogen gas for approximately ten minutes prior to the introduction of the reactants. Methyl stearate (29.85 g; 0.1 moles) and methyl oleate (29.65 g; 0.1 moles) were added and stirred at 50° C. with nitrogen gas sparging under a vacuum of about 0.5 mm Hg for one-half hour. Sucrose octaacetate (16.97 g; 0.025 moles) was then added and stirred under the same conditions for an additional one-half hour. The molar ratio of fatty acid methyl esters to sucrose octaacetate was about 8 to 1. Calcium hydride (0.38 g; 0.5 weight percent) was added and the reaction was allowed to continue for about 20 minutes at about 80° C. and a pressure of about 1 mm Hg. After about 20 minutes, sodium methoxide (1.15 g; 1.5 weight percent) was added. The reaction mixture was stirred and heated to 110° C. at about 1 mm Hg pressure for about four hours with continuous nitrogen gas sparging to remove the by-product ester. All reactants were essentially anhydrous; the sucrose octaacetate was freeze dried prior to use to remove residual moisture and free acetic acid. The yield of the sucrose polyester was about 69 percent as determined by HPLC. The sucrose polyester product was significantly lighter in color than products made under similar conditions using sodium methoxide catalyst without the calcium hydride co-catalyst.

EXAMPLE 7

A reaction vessel was flushed with dry nitrogen gas for approximately ten minutes prior to the introduction of the reactants. Methyl stearate (29.85 g; 0.1 moles) and methyl oleate (29.65 g; 0.1 moles) were added and stirred at 50° C. with nitrogen gas sparging under a vacuum of about 250 mm Hg for one-half hour. Sucrose octaacetate (16.97 g; 0.025 moles) was then added and stirred under the same conditions for an additional one-half hour. The molar ratio of fatty acid methyl esters to sucrose octaacetate was about 8 to 1. Sodium hypophosphite hydrate ($NaH_2PO_2 \cdot H_2O$; 0.62 g; 0.79 weight percent) was added and the reaction was heated to 110° C. at a pressure of about 250 mm Hg for 4 hours. The reaction mixture was cooled to room temperature and stored under nitrogen overnight. The next morning, the reaction mixture was again heated to 110° C. at a pressure of about 250 mm Hg with nitrogen sparging. Sodium methoxide (1.53 g; 2 weight percent) was then added and the reaction continued for 7 hours at 110° C. and about 250 mm Hg pressure with continuous nitrogen sparging. The sucrose octaacetate was freeze dried prior to use to remove residual moisture and free acetic acid. The yield of the sucrose polyester was about 89.2 percent as determined by HPLC. The sucrose polyester product was a dark brown color.

That which is claimed is:

1. A method for making a saccharide fatty acid polyester comprising:
    (1) esterifying hydroxyl groups of a saccharide to form a lower acyl ester saccharide having at least 50 percent of the hydroxyl groups esterified;
    (2) treating the lower acyl ester saccharide to reduce the level of free organic acid therein to less than about 0.25 weight percent;
    (3) mixing the treated lower acyl ester saccharide, a fatty acid lower alkyl ester, and an alkali metal alkoxide catalyst under essentially anhydrous conditions to form a reaction mixture; and
    (4) heating the reaction mixture to about 95° to 125° C., while removing a non-fatty acid-containing lower alkyl ester by-product from the reaction mixture, for a time sufficient to form the saccharide fatty acid polyester.

2. A method as defined in claim 1 wherein the lower acyl ester saccharide formed in step (1) has essentially all of the hydroxyl groups esterified.

3. A method as defined in claim 2, wherein the non-fatty acid-containing lower alkyl ester by-product is continuously removed from the reaction mixture by drawing a vacuum of less than about 250 mm Hg over the reaction mixture.

4. A method as defined in claim 3, wherein the vacuum is less than about 15 mm Hg.

5. A method as defined in claim 3, wherein the reaction mixture in step (4) is contacted with a dry inert gas to assist in the removal of the non-fatty acid-containing lower alkyl by-product from the reaction mixture.

6. A method as defined in claim 2, wherein the non-fatty acid-containing lower alkyl ester by-product is continuously removed from the reaction mixture by sparging with a dry inert gas.

7. A method as defined in claim 2, wherein the catalyst is selected from the group consisting of sodium methoxide, potassium methoxide, sodium ethoxide, potassium ethoxide, sodium t-butoxide, and potassium t-butoxide.

8. A method as defined in claim 7, wherein the saccharide is sucrose.

9. A method as defined in claim 8, wherein the lower acyl ester saccharide is sucrose with eight ester groups of the general formula —OOCR, where R is an aliphatic group containing from 1 to 6 carbon atoms, and the fatty acid lower alkyl ester is selected from the group consisting of methyl stearate, methyl oleate, methyl palmitate, methyl laurate, methyl linoleate, and mixtures thereof.

10. A method as defined in claim 9, wherein the lower acyl ester saccharide is sucrose octaacetate.

11. A method as defined in claim 2, wherein a co-catalyst selected from the group consisting of alkaline earth hydrides and alkali metal hypophosphites is used in combination with the alkali metal alkoxide catalyst.

12. A method as defined in claim 11, wherein the co-catalyst is calcium hydride or sodium hypophosphite.

13. A method for making a saccharide fatty acid polyester comprising:
(1) mixing a lower acyl ester saccharide wherein at least 50 percent of the available hydroxyl groups in the saccharide are esterified, a fatty acid lower alkyl ester, and an alkali metal alkoxide catalyst under essentially anhydrous conditions to form a reaction mixture, wherein the lower acyl ester saccharide has less than about 0.25 weight percent free organic acid; and
(2) heating the reaction mixture to about 95° to 125° C., while removing a non-fatty acid-containing lower alkyl ester by-product from the reaction mixture, for a time sufficient to form the saccharide fatty acid polyester.

14. A method as defined in claim 12 wherein, for the lower acyl ester saccharide, essentially all of the available hydroxyl groups in the saccharide are esterified.

15. A method as defined in claim 14, wherein the non-fatty acid-containing lower alkyl ester by-product is continuously removed from the reaction mixture by drawing a vacuum of less than about 250 mm Hg over the reaction mixture.

16. A method as defined in claim 15, wherein the vacuum is less than about 15 mm Hg.

17. A method as defined in claim 15, wherein the reaction mixture in step (2) is contacted with a dry inert gas to assist in the removal of the non-fatty acid-containing lower alkyl by-product from the reaction mixture.

18. A method as defined in claim 14, wherein the non-fatty acid-containing lower alkyl ester by-product is continuously removed from the reaction mixture by sparging with a dry inert gas.

19. A method as defined in claim 2, wherein the catalyst is selected from the group consisting of sodium methoxide, potassium methoxide, sodium ethoxide, potassium ethoxide, sodium t-butoxide, and potassium t-butoxide.

20. A method as defined in claim 19, wherein the lower acyl ester saccharide is a lower acyl ester sucrose.

21. A method as defined in claim 20, wherein the lower acyl ester saccharide is sucrose with eight ester groups of the general formula —OOCR, where R is an aliphatic group containing from 1 to 6 carbon atoms, and the fatty acid lower alkyl ester is selected from the group consisting of methyl stearate, methyl oleate, methyl palmitate, methyl laurate, methyl linoleate, and mixtures thereof.

22. A method as defined in claim 21, wherein the lower acyl ester saccharide is sucrose octaacetate.

23. A method as defined in claim 14, wherein a co-catalyst selected from the group consisting of alkaline earth hydrides and alkali metal hypophosphites is used in combination with the alkali metal alkoxide catalyst.

24. A method as defined in claim 23, wherein the co-catalyst is calcium hydride or sodium hypophosphite.

25. A method for making a saccharide fatty acid polyester comprising:
(1) mixing a fatty acid lower alkyl ester and an alkali metal alkoxide catalyst under essentially anhydrous conditions to form a first reaction mixture;
(2) heating the first reaction mixture to about 50° to 125° C.;
(3) adding an essentially anhydrous lower acyl ester saccharide having less than about 0.25 weight percent free organic acid and having at least 50 percent of the available hydroxyl groups in the saccharide esterified to the first reaction mixture from step (2) to form a second reaction mixture; and
(4) heating the second reaction mixture to about 95° to 125° C., while removing a non-fatty acid-containing lower alkyl ester by-product from the second reaction mixture, for a time sufficient to form the saccharide fatty acid polyester.

26. A method as defined in claim 25 wherein the lower acyl ester saccharide has essentially all of the available hydroxyl groups in the saccharide esterified.

27. A method as defined in claim 26, wherein the non-fatty acid-containing lower alkyl ester by-product is continuously removed from the reaction mixture by drawing a vacuum of less than about 250 mm Hg over the reaction mixture.

28. A method as defined in claim 27, wherein the vacuum is less than about 15 mm Hg.

29. A method as defined in claim 27, wherein the reaction mixture in step (4) is contacted with a dry inert gas to assist in the removal of the non-fatty acid-containing lower alkyl by-product from the reaction mixture.

30. A method as defined in claim 26, wherein the non-fatty acid-containing lower alkyl ester by-product is continuously removed from the reaction mixture by sparging with a dry inert gas.

31. A method as defined in claim 26, wherein the catalyst is selected from the group consisting of sodium methoxide, potassium methoxide, sodium ethoxide, potassium ethoxide, sodium t-butoxide, and potassium t-butoxide.

32. A method as defined in claim 31, wherein the lower acyl ester saccharide is a lower acyl ester sucrose.

33. A method as defined in claim 29, wherein the lower acyl ester saccharide is sucrose with eight ester groups of the general formula —OOCR, where R is an aliphatic group containing from 1 to 6 carbon atoms, and the fatty acid lower alkyl ester is selected from the group consisting of methyl stearate, methyl oleate, methyl palmitate, methyl laurate, methyl linoleate, and mixtures thereof.

34. A method as defined in claim 33, wherein the lower acyl ester saccharide is sucrose octaacetate.

35. A method as defined in claim 26, wherein a co-catalyst selected from the group consisting of alkaline earth hydrides and alkali metal hypophosphites is used in combination with the alkali metal alkoxide catalyst.

36. A method as defined in claim 35, wherein the co-catalyst is calcium hydride or sodium hypophosphite.

37. A method for making a saccharide fatty acid polyester comprising:
(1) mixing a lower acyl ester saccharide having less than about 0.25 weight percent free organic acid and having at least 50 percent of the available hydroxyl groups in the saccharide esterified, a fatty acid lower alkyl ester, and an alkali metal alkoxide catalyst under essentially anhydrous conditions to form a reaction mixture; and
(2) heating the reaction mixture to about 95° to 125° C. for a time sufficient to form the saccharide fatty acid polyester, while removing a non-fatty acid-containing lower alkyl ester by-product from the reaction mixture by inert gas stripping.

38. A method as defined in claim 37 wherein the lower acyl ester saccharide has essentially all of the available hydroxyl groups in the saccharide esterified.

39. A method as defined in claim 38, wherein the catalyst is selected from the group consisting of sodium methoxide, potassium methoxide, sodium ethoxide, potassium ethoxide, sodium t-butoxide, and potassium t-butoxide.

40. A method as defined in claim 39, wherein the lower acyl ester saccharide is a lower acyl ester sucrose.

41. A method as defined in claim 40, wherein the lower acyl ester saccharide is sucrose with eight ester groups of the general formula —OOCR, where R is an aliphatic group containing from 1 to 6 carbon atoms, and the fatty acid lower alkyl ester is selected from the group consisting of methyl stearate, methyl oleate, methyl palmitate, methyl laurate, methyl linoleate, and mixtures thereof.

42. A method as defined in claim 41, wherein the lower acyl ester saccharide is sucrose octaacetate.

43. A method as defined in claim 42, wherein a co-catalyst selected from the group consisting of alkaline earth hydrides and alkali metal hypophosphites is used in combination with the alkali metal alkoxide catalyst.

44. A method as defined in claim 43, wherein the co-catalyst is calcium hydride or sodium hypophosphite.

* * * * *

UNITED STATES PATENT AND TRADEMARK OFFICE
CERTIFICATE OF CORRECTION

PATENT NO. : 5,424,420
DATED : June 13, 1995
INVENTOR(S) : Gerry Hasenhuettl et al.

It is certified that error appears in the above-indentified patent and that said Letters Patent is hereby corrected as shown below:

Column 13, line 52, change the dependency from "12" to --13--.

Column 14, line 3, change the dependency from "2" to --14--.

Column 15, line 3, change the dependency from "29" to --32--.

Signed and Sealed this

Third Day of October, 1995

Attest:

BRUCE LEHMAN

*Attesting Officer*     Commissioner of Patents and Trademarks